US005800807A

United States Patent [19]

Hu et al.

[11] Patent Number: 5,800,807
[45] Date of Patent: Sep. 1, 1998

[54] OPHTHALMIC COMPOSITIONS INCLUDING GLYCERIN AND PROPYLENE GLYCOL

[75] Inventors: Zhenze Hu; John Denick, both of Pittsford, N.Y.

[73] Assignee: Bausch & Lomb Incorporated, Rochester, N.Y.

[21] Appl. No.: 794,690

[22] Filed: Jan. 29, 1997

[51] Int. Cl.$^6$ .................................................. A61K 31/74
[52] U.S. Cl. ...................... 424/78.04; 514/912; 514/915
[58] Field of Search ...................... 424/78.04; 514/912, 514/915

[56] References Cited

U.S. PATENT DOCUMENTS

| | | | |
|---|---|---|---|
| 2,703,777 | 3/1955 | Feinstein et al. | 167/59 |
| 3,311,577 | 3/1967 | Rankin | 260/17 |
| 3,549,747 | 12/1970 | Krezanowski et al. | 424/78 |
| 3,767,788 | 10/1973 | Rankin | 424/78 |
| 3,767,789 | 10/1973 | Rankin | 424/78 |
| 3,856,919 | 12/1974 | Rankin | 424/78 |
| 3,907,985 | 9/1975 | Rankin | 424/78 |
| 3,920,810 | 11/1975 | Rankin | 424/80 |
| 3,947,573 | 3/1976 | Rankin | 424/80 |
| 3,987,163 | 10/1976 | Rankin | 424/78 |
| 4,013,576 | 3/1977 | Loshaek | 252/106 |
| 4,029,817 | 6/1977 | Blanco et al. | 424/329 |
| 4,039,662 | 8/1977 | Hecht et al. | 424/180 |
| 4,120,949 | 10/1978 | Baptla et al. | 424/80 |
| 4,131,651 | 12/1978 | Shah et al. | 424/78 |
| 4,409,205 | 10/1983 | Shively | 424/78 |
| 4,421,748 | 12/1983 | Traget et al. | 424/199 |
| 4,432,964 | 2/1984 | Shell et al. | 424/14 |
| 4,438,123 | 3/1984 | Smith | 424/270 |
| 4,470,965 | 9/1984 | Wolf et al. | 424/80 |
| 4,525,346 | 6/1985 | Stark | 424/80 |
| 4,626,292 | 12/1986 | Sherman | 134/26 |
| 4,744,980 | 5/1988 | Holly | 424/78 |
| 5,061,714 | 10/1991 | Tadokoro et al. | 514/309 |
| 5,106,615 | 4/1992 | Dikstein | 424/78.04 |
| 5,141,665 | 8/1992 | Sherman | 252/106 |
| 5,188,826 | 2/1993 | Chandrasekaran et al. | 424/78.04 |
| 5,264,449 | 11/1993 | Albaugh | 514/397 |
| 5,591,426 | 1/1997 | Dabrowski et al. | 424/78.04 |

OTHER PUBLICATIONS

"Tear Film Stability and Tear Surface Tension," *Current Eye Research*, vol. 8, No. 5, 1989, pp. 507–515.

"Ophthalmic Drug Products for Over–the–Counter Human Use; Final Monograph", Fed. Reg., vol. 53, No. 43, Mar. 4, 1988.

*Primary Examiner*—Carlos Azpuru
*Attorney, Agent, or Firm*—Chris P. Konkol

[57] ABSTRACT

There are disclosed ophthalmic compositions having high water-binding properties which are useful as: moisturizing and lubricating (i.e. artificial tear) solutions, dry eye therapies, contact lens wetting and lubricating solutions, and as delivery vehicles for ophthalmic drugs. The subject compositions include glycerin in combination with propylene glycol. The subject compositions may further include cellulose derivatives, e.g. hydroxypropyl methyl cellulose, along with preservatives, e.g. benzylalkonium chloride, PHMB, sorbic acid, etc. Preferred compositions have at least 11% bound water, a pH from about 7.1 to 7.5, and an osmolality between about 280 to about 320 mOsm/Kg.

10 Claims, No Drawings

5,800,807

OPHTHALMIC COMPOSITIONS INCLUDING GLYCERIN AND PROPYLENE GLYCOL

FIELD OF THE INVENTION

The present invention is directed toward ophthalmic compositions, particularly those provided as buffered, aqueous solutions. The subject compositions are useful as: moisturizing and lubricating eye drops, delivery vehicles for ophthalmic drugs, and as contact lens wetting and lubricating solutions.

BACKGROUND

Ophthalmic compositions used for the treatment of "dry eye" symptoms include demulcents (or humectants) for lubricating mucous membrane surfaces and for relieving dryness and irritation. The term "demulcent", as used herein is intended to mean an agent, usually a water-soluble polymer, which is applied topically to the eye to protect and lubricate mucous membrane surfaces and relieve dryness and irritation. Within this meaning, the terms "humectant" and "wetting agent" are also commonly used. Furthermore, it will be understood that some constituents possess several functional attributes. For example, cellulose derivatives are common demulcents, but are also used as "viscosity increasing agents". Similarly, glycerin is a known demulcent but is also used as a "tonicity adjusting agent". Examples of the most widely used demulcents include: polyvinyl alcohol, polyvinyl pyrrolidone, cellulose derivatives and polyethylene glycol.

"Over-the-counter" use of demulcents within ophthalmic compositions is regulated by the US Food & Drug Administration. For example, the Federal Register (21 CFR Part 349) entitled *Ophthalmic Drug Products for Over-the-Counter Use: Final Monograph* list the accepted demulcents along with appropriate concentration ranges for each. Specifically, §349.12 list the following approved "monograph" demulcents: (a) cellulose derivatives: (1) carboxymethylcellulose sodium, (2) hydroxyethyl cellulose, (3) hydroxypropyl methylcellulose, methylcellulose, (b) dextran 70, (c) gelatin, (d) polyols, liquid: (1) glycerin, (2) polyethylene glycol 300, (3) polyethylene glycol 400, (4) polysorbate 80, (5) propylene glycol (e) polyvinyl alcohol, and (f) povidone (polyvinyl pyrrolidone). §349.30 further provides that in order to fall within the monograph, no more than three of the above-identified demulcents may be combined.

Specific examples of known ophthalmic compositions including various demulcents are provided below.

U.S. Pat. No. 5,591,426 to Dabrowski et al. discloses a ophthalmic solution useful as an artificial tear. The reference includes a specific example of a borate buffered, preserved (e.g. benzalkonium chloride), aqueous solution including the following three demulcents: 1) glycerin, 2) polyvinyl pyrrolidone, and 3) a cellulose derivative, e.g. hydroxypropyl methyl cellulose.

U.S. Pat. No. 5,106,615 to Dikstein discloses isotonic humectant eyedrops including glycerin, polyethylene glycol, or propylene glycol with an anionic polymer such as Carbomer 941.

U.S. Pat. No. 2,703,777 to Feinstein et al. generally describes a preserved, buffered, isotonic ophthalmic gel including: 1) a humectant, preferably glycerin (sorbitol and propylene glycol are also listed); 2) methyl cellulose, and 3) polyethylene glycol.

U.S. Pat. No. 4,029,817 to Blanco et al. discloses a contact lens preserving solution including propylene glycol in combination with polysorbate 80 and/or polyvinyl pyrrolidone. Similarly, U.S. Pat. No. 5,141,665 to Sherman discloses a contact lens cleaning, wetting and storing solution which includes propylene glycol as a wetting agent. Also, U.S. Pat. No. 4,525,346 to Stark discloses a borate buffered, preserved contact lens solution including propylene glycol.

U.S. Pat. Nos. 3,767,788; 3,767,789; 3,856,919; 3,907,985; 3,920,810; 3,947,573; 3,987,163 all to Billy Rankin disclose ophthalmic solutions for the treatment of "dye eye". These references generally teach the use of polyethylene oxide, polystyrene sulfonate, and polyacrylamide, with polyalkylene glycols, e.g. polyethylene glycol or propylene glycol. These references include specific example solutions including several demulcents combined with one another; namely, 1) polyethylene glycol, 2) polyvinyl pyrrolidone and a 3) cellulose derivative, e.g. hydroxy ethyl cellulose.

U.S. Pat. No. 3,549,747 to Krezanoski et al. discloses a preserved contact lens wetting solution including polyvinyl alcohol with a cellulose derivative, e.g. hydroxy ethyl cellulose. Similarly, U.S. Pat. No. 4,131,651 to Shah et al. discloses an ophthalmic solution for the treatment of dry eye which includes polyvinyl alcohol with a cellulose derivative. U.S. Pat. No. 4,120,949 to Bapatla et al. discloses a preserved ophthalmic solution including 1) polyvinyl alcohol, 2) polyvinylpyrrolidone, and 3) one or more cellulose derivatives. Also similarly, U.S. Pat. No. 4,409,205 to Shively discloses a specific example of a preserved ophthalmic solution including: polyvinyl alcohol, polyethylene glycol 6000, and dextrose. This reference also generally discloses the use of tonicity adjusting agents selected from the group of: mannitol, sorbitol, dextrose, sucrose, urea, and glycerin.

New ophthalmic compositions are sought which provide greater relief from dryness and irritation. In this regard, compositions capable of binding higher amounts of water have been identified by applicants as being particularly preferred. Furthermore, it desired to accomplish these improvements while using approved monograph demulcents.

SUMMARY OF THE INVENTION

The present invention is an ophthalmic composition comprising glycerin and propylene glycol. It has been discovered that propylene glycol and glycerin are capable of binding significantly greater amounts of water than other demulcents, as will be described below.

In one preferred embodiment, the subject composition is provided as a buffered, aqueous solution which includes a third demulcent, preferably a cellulose derivative. The subject composition may be unpreserved (provided in a single dose format), or may be preserved, e.g. with benzylalkonium chloride, PHMB, sorbic acid, etc.

DETAILED DESCRIPTION OF THE INVENTION

As previously described, the subject composition finds particular utility as a moisturizing and lubricating eye drop (i.e. an artificial tear solution), a delivery vehicle for ophthalmic drugs, and as a contact lens wetting and lubricating solution. In most of these applications, the subject composition is provided as a buffered aqueous solution. Such a solution typically has a viscosity from about 1 to about 50 cps. As a solution, the subject composition is usually dispensed in the eye in the form of an eye drop. It should be understood, however, that the subject composition may also be formulated as a viscous liquid (i.e. viscosities from 50 to several thousand cps), gel, or ointment. Furthermore, in some contact lens related embodiments, lenses may be soaked or otherwise exposed to the subject composition prior to wear.

The present ophthalmic compositions include glycerin and propylene glycol. In addition to these two demulcents, other demulcents may also be used. However, the FDA regulations limit the number of demulcents which may be used together in over-the-counter ophthalmics, to three demulcents. In light of this regulation, and in an effort to simplify formulations and reduce undesirable interaction among constituents, it may be desirable to limit the number of demulcents used in a given composition. Thus, in several preferred embodiments of the subject invention, the only demulcents used are glycerin and propylene glycol, or alternatively glycerin, propylene glycol and one other demulcent, preferably a cellulose derivative. Cellulose derivatives are commonly used to increase viscosity, and as such, offer other advantages. Specific cellulose derivatives include: hydroxypropyl methyl cellulose, carboxymethyl cellulose, methyl cellulose, hydroxyethyl cellulose, etc. In these embodiments, other demulcents such as polyvinyl pyrrolidone, polyvinyl alcohol, polyethylene glycol, and other components such as polyethylene oxide, and polyacrylic acid are specifically excluded.

In still other embodiments, other or additional demulcents may be used in combination with glycerin and propylene glycol. For example, polyvinyl pyrrolidone, polyvinyl alcohol, may also be used.

The demulcents used in the present invention are used in effective amounts (i.e. "demulcifing amounts") for providing a demulcifing effect, i.e. sufficient to lubricating mucous membrane surfaces and to relieve dryness and irritation. The specific quantities of demulcents used in the present invention will vary depending upon the application; however, typically ranges of several demulcents are provided: glycerin: from about 0.2 to about 1.5%, but preferably about 1% (w/w); propylene glycol: from about 0.2 to about 1.5%, but preferably about 1% (w/w); cellulose derivative: from about 0.2 to about 3%, but preferably about 0.5% (w/w). If additional demulcents are used, they are typically used in quantities specified in the over-the-counter monograph, cited above. A preferred cellulose derivative is pharmaceutical grade hydroxypropyl methylcellulose (BPMC), such as Methocel E 15 LV—premium, available from Dow Chemical Company.

When used, any pharmaceutically acceptable buffer system may be utilized; however, a preferred buffer system is provided by sodium borate and boric acid in amounts necessary to produce a pH of about 6.0 to about 8.0, but more preferably from about 7.1 to about 7.5.

The composition may be designed for a variety of osmolalities, but in most applications, iso-osmolal (with respect to the fluids of the eye) compositions are preferred. Osmolalities typically range from about 175 to about 330 mOsm/kg, but more preferably from about 280 to about 320 mOsm/kg. The osmolality of the solution may be adjusted by means of well known osmolality adjusting agents, e.g. sodium chloride and potassium chloride, and monosaccharides.

As previously indicated, the subject composition may include a preservative in an amount effective to preserve the solution. As is known in the art, the amount of preservative required will vary upon the specific preservative and the application, e.g. moisturizing eye drop, contact lens solution, etc. For non-contact lens applications, benzalkonium chloride (BAK) is a preferred preservative typically used in concentrations from about 0.01 to about 0.10%(w/w). BAK is a well known preservative which comprises a mixture of alkyldimethyl benzylammonium chlorides. For contact lens applications, other preservative are more preferred, such as sorbic acid, PHMB, and other polyquats. Alternatively, the subject compositions may be preservative-free.

The composition may include a number of additional components. For example, the solution may include edetate disodium as a co-preservative and/or chelating agent.

EXAMPLE I

As an illustration of the present invention, a preferred moisturizing eye drop formulation is provided below.

TABLE I

| Constituent | % w/w |
|---|---|
| glycerin | 1.0 |
| propylene glycol | 0.5 |
| hydroxypropylmethyl cellulose (HPMC) | 1.0 |
| boric acid | 0.300 |
| sodium borate | 0.035 |
| sodium chloride (NaCl) | 0.096 |
| potassium chloride (KCl) | 0.097 |
| edetate disodium (EDTA) | 0.030 |
| benzalkonium chloride (BAK) (50%) | 0.021 |
| purified water | q.s. to 100% |

The formulation was prepared by adding each of NaCl, KCl, sodium borate, boric acid, EDTA and HPMC (Type E15-LV Premium) sequentially to a volume of heated water (80°–90° C.) that amounted to 70–85% of the final batch volume. This addition was accomplished under constant agitation and each component was allowed to dissolve or disperse before adding the next. The resulting solution was mixed for about 30 minutes and maintained at a temperature of about 85° C. With continued agitation, the batch was cooled to 50° C. (+/–5° C.), at which point propylene glycol, glycerin, and BAK (50% solution) were each sequentially added to the solution. The batch was cooled under agitation to about 20° C. (+/–5° C). The pH of the solution was then adjusted to about 7.1 to about 7.5 using increments of either 1 N NaOH or 1 N HCl, and was then brought to final volume with 20 –30° C. water and mixed for at least 15 minutes. The BAK concentration is finally adjusted to a 95–110 ppm range.

EXAMPLE II

The water-binding capacity of several demulcents were evaluated based upon the freezably water fraction of a 10% demulcent solution. Samples were evaluated using differential scanning calorimetry (DSC), utilizing a TA instrument DSC 912 with a 2100 controller. The instrument was calibrated using indium metal and HPLC grade water for the upper and lower temperatures corrections, respectively.

The indium metal calibration was completed as follows. An aluminum sample pan and cover were weighed. Once the pan weight was zeroed, a piece of indium metal was placed in the pan and covered and weighed. Approximately 10 mg of indium was used for both cells. The aluminum pan was hermetically sealed and placed on the appropriate cell head, A or B. An empty aluminum pan was hermetically sealed and placed on the reference head. Nitrogen gas was purged through the cell entering through the vacuum and cooling ports at a fixed rate (50 on the scale of a Gilmont flowmeter). The cell was closed and the following temperature program was used:

1. equilibrate at 130° C.;
2. isothermal for 4.0 minutes;
3. ramp 1.00° C./minute to 180° C.;
4. isothermal for 2.00 minutes.

The HPLC water calibration was completed as follows. Two water samples were prepared in a fashion similar to that as described above. Approximately 10 µl of HPLC grade water was injected into a zeroed pan assembly. The weight was obtained with the cover on the pan so that the sample did not evaporate while being weighed. The following temperature program was used for all water samples.

1. Equilibrate at −20° C.;
2. ramp 1.00° C./minutes to 20.0° C.

Indium endotherms were integrated between 156.3° C. and 158.3° C. Water endotherms were integrated from −1° C. to 5° C. The onset of the melt endotherms were averaged from cell A and B. The average melt temperature for the indium and water calibration samples were imputed into the temperature calibration. Cell constants were calculated for Cell A and B using the delta H values determined for the water samples. The literature value for the heat of fusion of water is 333.6 J/g. Cell constants were calculated by dividing this value by the delta H value obtained on that cell. These values were then inputted into the module parameters.

The demulcent samples were tested in a similar manner as the water calibration samples described above. Three runs for each sample were completed. The demulcent sample endotherms were integrated between approximately −15° C. and 7° C. The results of the evaluation are provided in Table II, below.

TABLE II

| DEMULCENT | grams bound water per gram of dry demulcent |
|---|---|
| methylcellulose | 1.237 |
| dextran 70 | 0.683 |
| hydroxypropyl methyl cellulose | 1.138 |
| polyvinylpyrrolidone | 1.370 |
| carboxymethylcellulose sodium | 0.947 |
| hydroxyethylcellulose | 1.168 |
| polyvinyl alcohol | 0.956 |
| polysorbate 80 | 0.982 |
| polyethylene glycol 300 | 1.959 |
| polyethylene glycol 400 | 1.907 |
| glycerin | 2.212 |
| gelatin | 1.340 |
| propylene glycol | 2.756 |

As indicated from the data of Table II, propylene glycol and glycerin had far greater water-binding capacities than all other demulcent tested. This result was unexpected, particularly given the infrequent use of propylene glycol as a demulcent in the art. By combining glycerin and propylene glycol together as demulcents, it is possible to prepare improved ophthalmic compositions having at least 11%, and preferably about 13% percent bound water as defined by Formula I below. This is has been accomplished while complying with the monograph requirements.

FORMULA I

Percent Bound Water=Percent Total Water—100 (delta $H_{sample}$/delta $H_{water}$)

We claim:

1. An ophthalmic composition comprising:
   (a) from about 0.2 to 1.5 weight percent of glycerin, and
   (b) from about 0.2 to 1.5 weight percent of propylene glycol, wherein said solution has an osmolality of between about 175 and 330 mOsm/kg and a pH from 6.0 to 8.0.

2. The composition of claim 1 including at least one of: a cellulose derivative, dextran, gelatin, polyethylene glycol, polysorbate, polyvinyl alcohol and polyvinyl-pyrrolidone.

3. The composition of claim 2 including at least one cellulose derivative selected from the group: hydroxypropyl methyl cellulose, carboxymethyl cellulose, methyl cellulose, and hydroxyethyl cellulose.

4. The composition of claim 1 including a preservative.

5. The composition of claim 4 including at least one preservative selected from the group: benzylalkonium chloride, polyquat, PHMB, and sorbic acid.

6. The composition of claim 1 having a pH from about 7.1 to about 7.5, an osmolality between about 280 to about 320 mOsm/Kg, and at least about 11 percent bound water.

7. An ophthalmic solution useful as an artificial tear comprising:
   (a) from about 0.2 to about 1.5 weight percent of glycerin,
   (b) from about 0.2 to about 1.5 weight percent of propylene glycol,
   (c) from about 0.2 to 3.0% of a cellulose derivative, and
   (d) a borate buffer, and
   wherein said solution has an osmolality between about 280 to about 320 MOsm/Kg, and a pH from about 7.1 to about 7.5.

8. The solution of claim 7 which excludes polyvinylpyrrolidone, polyvinyl alcohol, polyethylene glycol, and polyethylene oxide, polyacrylic acid, anionic polymers.

9. A method for moisturizing or lubricating the eye by contacting the eye with an ophthalmic composition comprising:
   (a) from about 0.2 to 1.5 weight percent of glycerin, and
   (b) from about 0.2 to 1.5 weight percent of propylene glycol, wherein said solution has an osmolality of between about 175 and 330 mOsm/kg and a pH from 6.0 to 8.0.

10. An ophthalmic composition comprising a combination of demulcents consisting essentially of:
   (a) from about 0.2 to 1.5 weight percent of glycerin, and
   (b) from about 0.2 to 1.5 weight percent of propylene glycol, wherein said solution has an osmolality of between about 175 and 330 mOsm/kg and a pH from 6.0 to 8.0.

* * * * *

UNITED STATES PATENT AND TRADEMARK OFFICE
CERTIFICATE OF CORRECTION

| | | |
|---|---|---|
| PATENT NO. | : 5,800,807 | |
| APPLICATION NO. | : 08/794690 | |
| DATED | : September 1, 1998 | |
| INVENTOR(S) | : Zhenze Hu et al. | |

It is certified that error appears in the above-identified patent and that said Letters Patent is hereby corrected as shown below:

In Col. 3, line 61
replace "solution"
with "composition."

In Col. 6, line 12
replace "solution"
with "composition."

Signed and Sealed this

Thirtieth Day of October, 2012

David J. Kappos
*Director of the United States Patent and Trademark Office*